United States Patent
Hendriksen et al.

(10) Patent No.: US 7,699,867 B2
(45) Date of Patent: Apr. 20, 2010

(54) REMOVABLE VENA CAVA FILTER FOR REDUCED TRAUMA IN COLLAPSED CONFIGURATION

(75) Inventors: Per Hendriksen, Herlufmagle (DK); Allan G. Hemmingsen, Jystrup (DK); Arne Molgaard-Nielsen, Oesterbro (DK); Thomas A. Osborne, Bloomington, IN (US); Rolf Gunther, Aachen (DE)

(73) Assignees: Cook Incorporated, Bloomington, IN (US); William Cook Europe APS, Bjaeverskov (DK)

( * ) Notice: Subject to any disclaimer, the term of this patent is extended or adjusted under 35 U.S.C. 154(b) by 491 days.

(21) Appl. No.: 11/108,248

(22) Filed: Apr. 18, 2005

(65) Prior Publication Data
US 2005/0267512 A1 Dec. 1, 2005

Related U.S. Application Data

(60) Provisional application No. 60/562,943, filed on Apr. 16, 2004, provisional application No. 60/562,813, filed on Apr. 16, 2004, provisional application No. 60/562,909, filed on Apr. 16, 2004, provisional application No. 60/563,176, filed on Apr. 16, 2004.

(51) Int. Cl.
*A61M 29/00* (2006.01)
(52) U.S. Cl. .................................. 606/200
(58) Field of Classification Search ............... 606/108, 606/200, 127, 159; 623/1.11; 604/104–107
See application file for complete search history.

(56) References Cited

U.S. PATENT DOCUMENTS

| | | |
|---|---|---|
| 2,281,448 A | 4/1942 | Mathey |
| 3,137,298 A | 6/1964 | Glassman |
| 3,174,851 A | 3/1965 | Buehler |
| 3,334,629 A | 8/1967 | Cohn |

(Continued)

FOREIGN PATENT DOCUMENTS

DE 003417738 11/1985

(Continued)

OTHER PUBLICATIONS

Morris Simon, M.D. at al., A Vena Cava Filter Using Thermal Shape Memory Alloy, Oct. 1977, 89-94.

(Continued)

*Primary Examiner*—Todd E Manahan
*Assistant Examiner*—Lindsey Bachman
(74) *Attorney, Agent, or Firm*—Brinks Hofer Gilson & Lione

(57) ABSTRACT

The present invention provides a removable vena cava filter for capturing thrombi in a blood vessel. The filter comprises a plurality of primary struts having first ends attached together along a longitudinal axis. Each primary strut has an arcuate segment extending from the first end to an anchoring hook. The primary struts are configured to move between an expanded state for engaging the anchoring hooks with the blood vessel and a collapsed state for filter retrieval or delivery. Each primary strut are configured to cross another primary strut along the longitudinal axis in the collapsed state such that the arcuate segments occupy a first diameter greater than a second diameter occupied by the anchoring hooks in the collapsed state for filter retrieval or delivery.

18 Claims, 7 Drawing Sheets

U.S. PATENT DOCUMENTS

| | | | |
|---|---|---|---|
| 3,540,431 A | 11/1970 | Mobin-Uddin | |
| 3,868,956 A | 3/1975 | Alfidi et al. | |
| 3,952,747 A | 4/1976 | Kimmell, Jr. | |
| 4,425,908 A * | 1/1984 | Simon | 128/899 |
| 4,494,531 A | 1/1985 | Gianturco | |
| 4,619,246 A | 10/1986 | Molgaard-Nielsen et al. | |
| 4,643,184 A | 2/1987 | Mobin-Uddin | |
| 4,655,771 A | 4/1987 | Wallsten | |
| 4,665,906 A | 5/1987 | Jervis | |
| 4,688,553 A | 8/1987 | Metals | |
| 4,727,873 A | 3/1988 | Mobin-Uddin | |
| 4,759,757 A | 7/1988 | Pinchuk | |
| 4,781,177 A * | 11/1988 | Lebigot | 128/897 |
| 4,793,348 A | 12/1988 | Palmaz | |
| 4,817,600 A * | 4/1989 | Herms et al. | 606/198 |
| 4,830,003 A | 5/1989 | Wolff et al. | |
| 4,832,055 A | 5/1989 | Palestrant | |
| 4,856,516 A | 8/1989 | Hillstead | |
| 4,873,978 A | 10/1989 | Ginsburg | |
| 4,943,297 A | 7/1990 | Saveliev et al. | |
| 4,950,227 A | 8/1990 | Savin et al. | |
| 4,954,126 A | 9/1990 | Wallsten | |
| 4,957,501 A | 9/1990 | Lahille et al. | |
| 4,969,891 A | 11/1990 | Gewertz | |
| 4,990,156 A | 2/1991 | Lefebvre | |
| 5,037,377 A | 8/1991 | Alonso | |
| 5,059,205 A | 10/1991 | El-Nounou et al. | |
| 5,061,275 A | 10/1991 | Wallsten et al. | |
| 5,067,957 A | 11/1991 | Jervis | |
| 5,071,407 A | 12/1991 | Termin et al. | |
| 5,108,418 A | 4/1992 | Lefebvre | |
| 5,108,419 A | 4/1992 | Reger et al. | |
| 5,133,733 A | 7/1992 | Rasmussen et al. | |
| 5,135,516 A | 8/1992 | Sahatjian et al. | |
| 5,147,379 A | 9/1992 | Sabbaghian et al. | |
| 5,152,777 A | 10/1992 | Goldberg et al. | |
| 5,160,342 A | 11/1992 | Reger et al. | |
| 5,190,546 A | 3/1993 | Jervis | |
| 5,217,484 A | 6/1993 | Marks | |
| 5,221,261 A | 6/1993 | Termin et al. | |
| 5,224,953 A | 7/1993 | Morgentaler | |
| 5,234,458 A | 8/1993 | Metais | |
| 5,242,462 A | 9/1993 | El-Nounou et al. | |
| 5,300,086 A | 4/1994 | Gory et al. | |
| 5,304,121 A | 4/1994 | Sahatjian | |
| 5,304,200 A | 4/1994 | Spaulding | |
| 5,324,304 A * | 6/1994 | Rasmussen | 606/200 |
| 5,329,942 A | 7/1994 | Gunther et al. | |
| 5,344,427 A | 9/1994 | Cottenceau et al. | |
| 5,350,398 A | 9/1994 | Pavcnik et al. | |
| 5,370,657 A | 12/1994 | Irie | |
| 5,375,612 A | 12/1994 | Cottenceau et al. | |
| 5,382,261 A | 1/1995 | Palmaz | |
| 5,383,887 A | 1/1995 | Nadal | |
| 5,405,377 A | 4/1995 | Cragg | |
| 5,413,586 A | 5/1995 | Dibie et al. | |
| 5,421,832 A | 6/1995 | Lefebvre | |
| 5,476,508 A | 12/1995 | Amstrup | |
| 5,527,338 A | 6/1996 | Purdy | |
| 5,540,712 A | 7/1996 | Kleshinski et al. | |
| 5,549,626 A | 8/1996 | Miller et al. | |
| 5,549,629 A | 8/1996 | Thomas et al. | |
| 5,601,595 A | 2/1997 | Smith | |
| 5,626,605 A | 5/1997 | Irie et al. | |
| 5,630,801 A | 5/1997 | Roussigne et al. | |
| 5,634,942 A | 6/1997 | Chevillon et al. | |
| 5,649,906 A | 7/1997 | Gory et al. | |
| 5,649,953 A | 7/1997 | Lefebvre | |
| 5,669,933 A | 9/1997 | Simon et al. | |
| 5,681,347 A | 10/1997 | Cathcart et al. | |
| 5,683,411 A | 11/1997 | Kavteladze et al. | |
| 5,695,519 A | 12/1997 | Summers et al. | |
| 5,709,704 A | 1/1998 | Nott et al. | |
| 5,720,764 A | 2/1998 | Naderlinger | |
| 5,725,550 A | 3/1998 | Nadal | |
| 5,746,767 A | 5/1998 | Smith | |
| 5,755,778 A | 5/1998 | Kleshinski | |
| 5,755,790 A | 5/1998 | Chevillon et al. | |
| 5,776,162 A | 7/1998 | Kleshinski | |
| 5,800,457 A | 9/1998 | Gelbfish | |
| 5,800,525 A | 9/1998 | Bachinski et al. | |
| 5,807,398 A | 9/1998 | Shaknovich | |
| 5,810,874 A | 9/1998 | Lefebvre | |
| 5,836,968 A * | 11/1998 | Simon et al. | 606/200 |
| 5,836,969 A | 11/1998 | Kim et al. | |
| 5,843,244 A | 12/1998 | Pelton et al. | |
| 5,853,420 A | 12/1998 | Chevillon et al. | |
| 5,895,399 A | 4/1999 | Barbut et al. | |
| 5,902,317 A | 5/1999 | Kleshinski et al. | |
| 5,916,235 A | 6/1999 | Guglielmi | |
| 5,928,260 A | 7/1999 | Chin et al. | |
| 5,928,261 A | 7/1999 | Ruiz | |
| 5,932,035 A | 8/1999 | Koger et al. | |
| 5,938,683 A | 8/1999 | Lefebvre | |
| 5,951,585 A | 9/1999 | Cathcart et al. | |
| 5,961,546 A | 10/1999 | Robinson et al. | |
| 5,976,172 A | 11/1999 | Homsma et al. | |
| 5,984,947 A | 11/1999 | Smith | |
| 6,007,557 A | 12/1999 | Ambrisco et al. | |
| 6,007,558 A | 12/1999 | Ravenscroft et al. | |
| 6,013,093 A | 1/2000 | Nott et al. | |
| 6,077,274 A | 6/2000 | Ouchi et al. | |
| 6,080,178 A | 6/2000 | Meglin | |
| 6,086,610 A | 7/2000 | Duerig et al. | |
| 6,126,673 A | 10/2000 | Kim et al. | |
| 6,129,755 A | 10/2000 | Mathis et al. | |
| 6,146,404 A | 11/2000 | Kim et al. | |
| 6,152,144 A | 11/2000 | Lesh et al. | |
| 6,156,055 A | 12/2000 | Ravenscroft | |
| 6,156,061 A | 12/2000 | Wallace et al. | |
| 6,179,851 B1 | 1/2001 | Barbut et al. | |
| 6,179,859 B1 | 1/2001 | Bates et al. | |
| 6,179,861 B1 | 1/2001 | Khosravi et al. | |
| 6,193,739 B1 | 2/2001 | Chevillon et al. | |
| 6,221,102 B1 | 4/2001 | Baker et al. | |
| 6,231,589 B1 | 5/2001 | Wessman et al. | |
| 6,241,738 B1 | 6/2001 | Dereume | |
| 6,241,746 B1 | 6/2001 | Bosma et al. | |
| 6,245,012 B1 | 6/2001 | Kleshinski | |
| 6,245,088 B1 | 6/2001 | Lowery | |
| 6,251,122 B1 | 6/2001 | Tsukernik | |
| 6,258,026 B1 | 7/2001 | Ravenscroft et al. | |
| 6,267,776 B1 | 7/2001 | O'Connell | |
| 6,273,900 B1 | 8/2001 | Nott et al. | |
| 6,273,901 B1 | 8/2001 | Whitcher et al. | |
| 6,277,139 B1 | 8/2001 | Levinson et al. | |
| 6,287,315 B1 | 9/2001 | Wijeratne et al. | |
| 6,287,329 B1 | 9/2001 | Duerig et al. | |
| 6,306,163 B1 | 10/2001 | Fitz | |
| 6,312,454 B1 | 11/2001 | Stockel et al. | |
| 6,312,455 B2 | 11/2001 | Duerig et al. | |
| 6,325,815 B1 | 12/2001 | Kusleika et al. | |
| 6,331,183 B1 | 12/2001 | Suon | |
| 6,342,062 B1 | 1/2002 | Suon et al. | |
| 6,342,063 B1 | 1/2002 | DeVries et al. | |
| 6,342,067 B1 | 1/2002 | Mathis et al. | |
| 6,346,116 B1 | 2/2002 | Brooks et al. | |
| 6,364,895 B1 | 4/2002 | Greenhalgh | |
| 6,391,044 B1 | 5/2002 | Yadav et al. | |
| 6,391,045 B1 | 5/2002 | Kim et al. | |
| 6,436,120 B1 | 8/2002 | Meglin | |
| 6,436,121 B1 | 8/2002 | Blom | |
| 6,447,530 B1 * | 9/2002 | Ostrovsky et al. | 606/200 |
| 6,461,370 B1 | 10/2002 | Gray et al. | |

| | | |
|---|---|---|
| 6,468,290 B1 | 10/2002 | Weldon et al. |
| 6,482,222 B1 | 11/2002 | Bruckheimer et al. |
| 6,485,502 B2 | 11/2002 | DonMichael et al. |
| 6,506,205 B2 | 1/2003 | Goldberg et al. |
| 6,511,503 B1 | 1/2003 | Burkett et al. |
| 6,517,559 B1 | 2/2003 | O'Connell |
| 6,527,962 B1 | 3/2003 | Nadal |
| 6,540,767 B1 | 4/2003 | Walak et al. |
| 6,551,342 B1 | 4/2003 | Shen et al. |
| 6,558,404 B2 | 5/2003 | Tsukernik |
| 6,569,183 B1 | 5/2003 | Kim et al. |
| 6,579,303 B2 | 6/2003 | Amplatz |
| 6,582,447 B1 | 6/2003 | Patel et al. |
| 6,589,266 B2 | 7/2003 | Whitcher et al. |
| 6,602,226 B1 | 8/2003 | Smith et al. |
| 6,616,680 B1 | 9/2003 | Thielen |
| 6,638,294 B1 | 10/2003 | Palmer |
| 6,652,558 B2 | 11/2003 | Patel et al. |
| 6,685,722 B1 * | 2/2004 | Rosenbluth et al. ......... 606/200 |
| 6,726,621 B2 | 4/2004 | Suon et al. |
| 7,297,000 B1 | 11/2007 | Bernard |
| 2001/0000799 A1 | 5/2001 | Wessman et al. |
| 2001/0011181 A1 | 8/2001 | DiMatteo |
| 2001/0023358 A1 | 9/2001 | Tsukernik |
| 2001/0034547 A1 | 10/2001 | Hall et al. |
| 2001/0034548 A1 | 10/2001 | Vrba et al. |
| 2001/0037126 A1 | 11/2001 | Stack et al. |
| 2001/0039432 A1 | 11/2001 | Whitcher et al. |
| 2002/0002401 A1 | 1/2002 | McGuckin, Jr. et al. |
| 2002/0016624 A1 | 2/2002 | Patterson et al. |
| 2002/0032460 A1 | 3/2002 | Kusleika et al. |
| 2002/0039445 A1 | 4/2002 | Abe et al. |
| 2002/0055767 A1 | 5/2002 | Forde et al. |
| 2002/0087187 A1 | 7/2002 | Mazzocchi et al. |
| 2002/0099431 A1 | 7/2002 | Armstrong et al. |
| 2002/0116024 A1 | 8/2002 | Goldberg et al. |
| 2002/0133217 A1 | 9/2002 | Sirhan et al. |
| 2002/0138097 A1 | 9/2002 | Ostrovsky et al. |
| 2002/0156520 A1 | 10/2002 | Boylan et al. |
| 2002/0161393 A1 | 10/2002 | Demond et al. |
| 2002/0169474 A1 | 11/2002 | Kusleika et al. |
| 2002/0169495 A1 | 11/2002 | Gifford et al. |
| 2002/0183782 A1 | 12/2002 | Tsugita et al. |
| 2002/0193827 A1 | 12/2002 | McGuckin, Jr. et al. |
| 2002/0193828 A1 | 12/2002 | Griffin et al. |
| 2002/0193874 A1 | 12/2002 | Crowley |
| 2003/0018343 A1 | 1/2003 | Mathis |
| 2003/0028238 A1 | 2/2003 | Burkett et al. |
| 2003/0040772 A1 | 2/2003 | Hyodoh et al. |
| 2003/0055481 A1 | 3/2003 | McMorrow |
| 2003/0069596 A1 | 4/2003 | Eskuri |
| 2003/0074019 A1 | 4/2003 | Gray et al. |
| 2003/0078614 A1 | 4/2003 | Salahieh et al. |
| 2003/0083692 A1 | 5/2003 | Vrba et al. |
| 2003/0097145 A1 | 5/2003 | Goldberg et al. |
| 2003/0105484 A1 | 6/2003 | Boyle et al. |
| 2003/0109897 A1 | 6/2003 | Walak et al. |
| 2003/0114880 A1 | 6/2003 | Hansen et al. |
| 2003/0125790 A1 | 7/2003 | Fastovsky et al. |
| 2003/0125793 A1 | 7/2003 | Vesely |
| 2003/0130681 A1 | 7/2003 | Ungs |
| 2003/0144686 A1 | 7/2003 | Martinez et al. |
| 2003/0153943 A1 | 8/2003 | Michael et al. |
| 2003/0153945 A1 | 8/2003 | Patel et al. |
| 2003/0163159 A1 | 8/2003 | Patel et al. |
| 2003/0176888 A1 | 9/2003 | O'Connell |
| 2003/0181922 A1 | 9/2003 | Alferness |
| 2004/0010282 A1 | 1/2004 | Kusleika |
| 2004/0158273 A1 | 8/2004 | Weaver et al. |
| 2004/0186510 A1 | 9/2004 | Weaver |
| 2004/0193209 A1 | 9/2004 | Pavcnik et al. |
| 2004/0230220 A1 | 11/2004 | Osborne et al. |
| 2005/0165441 A1 | 7/2005 | McGuckin, Jr. et al. |
| 2005/0165442 A1 | 7/2005 | Thinnes, Jr. et al. |
| 2005/0251199 A1 | 11/2005 | Osborne et al. |
| 2005/0267513 A1 | 12/2005 | Osborne et al. |
| 2005/0267514 A1 | 12/2005 | Osborne et al. |
| 2006/0069406 A1 | 3/2006 | Hendriksen et al. |
| 2006/0100660 A1 | 5/2006 | Osborne et al. |
| 2007/0005095 A1 | 1/2007 | Osborne et al. |

FOREIGN PATENT DOCUMENTS

| | | |
|---|---|---|
| DE | 3429850 A1 | 2/1986 |
| EP | 0270432 A1 | 6/1988 |
| EP | 0348295 | 12/1989 |
| EP | 0350043 A1 | 10/1990 |
| EP | 0430848 A1 | 6/1991 |
| EP | 0437121 A2 | 7/1991 |
| EP | 0462008 A1 | 12/1991 |
| EP | 0472334 A1 | 2/1992 |
| EP | 0701800 A1 | 3/1996 |
| FR | 2587901 | 4/1987 |
| FR | 2649884 | 1/1991 |
| FR | 2672487 | 8/1992 |
| GB | 2200848 A | 8/1988 |
| GB | 2200848 B | 8/1988 |
| SU | 835447 | 6/1981 |
| SU | 1103868 A | 7/1984 |
| SU | 955912 A | 2/1988 |
| WO | WO 91/04716 | 4/1991 |
| WO | WO 91/11972 | 8/1991 |
| WO | WO 95/08567 | 3/1995 |
| WO | WO 95/27448 | 10/1995 |
| WO | WO 96/17634 | 6/1996 |
| WO | WO 01/06952 A1 | 2/2001 |
| WO | WO 03/011188 A1 | 2/2003 |
| WO | WO 2004/049973 A1 | 6/2004 |
| WO | WO 2005/072645 A1 | 8/2005 |
| WO | WO2005/102210 A1 | 11/2005 |
| WO | WO 2005/102211 A1 | 11/2005 |
| WO | WO 2005/102212 A1 | 11/2005 |
| WO | WO 2005/102213 A1 | 11/2005 |
| WO | WO 2005/102214 A1 | 11/2005 |
| WO | WO 2006/036867 A1 | 4/2006 |

OTHER PUBLICATIONS

James Hansen, Metal That Remember, 44-47.
Morris Simon et al., Transvenous Devices for the Management of Pulmonary Emobolism, 1980, 112-121.
J.L. Kraimps et al., Annals of Vascular Surgery, Mar. 1992, 99-110.
Jean-Louis Kraimps, M.D. et al., Optimal Central Trapping (OPCETRA) Vena Cava Filter: Results of Experimental Studies, Nov. 1992, 697-699.
International Search Report—PCT/US2005/013322 (Sep. 23, 2005).
International Search Report—PCT/US2005/013323 (Sep. 23, 2005).
International Search Report—PCT/US2005/013158 (Oct. 7, 2005).
International Search Report—PCT/US2005/013281 (Oct. 7, 2005).
International Search Report—PCT/US2005/013160) (Sep. 22, 2005).
International Search Report—PCT/US2005/034350 (Feb. 10, 2006).
International Search Report; PCT US2005/04029;(Apr. 11, 2007).

* cited by examiner

US 7,699,867 B2

REMOVABLE VENA CAVA FILTER FOR REDUCED TRAUMA IN COLLAPSED CONFIGURATION

CROSS REFERENCE TO RELATED APPLICATIONS

This application claims the benefit of U.S. Provisional Application No. 60/562,943, filed on Apr. 16, 2004, entitled "REMOVABLE VENA CAVA FILTER FOR REDUCED TRAUMA IN COLLAPSED CONFIGURATION," the entire contents of which are incorporated herein by reference.

This application also claims the benefit of U.S. Provisional Application No. 60/562,813, filed on Apr. 16, 2004, entitled "REMOVABLE FILTER FOR CAPTURING BLOOD CLOTS," the entire contents of which are incorporated herein by reference.

This application also claims the benefit of U.S. Provisional Application No. 60/562,909, filed on Apr. 16, 2004, entitled "BLOOD CLOT FILTER WITH STRUTS HAVING AN EXPANDED REMEMBERED STATE," the entire contents of which are incorporated herein by reference.

This application also claims the benefit of U.S. Provisional Application No. 60/563,176, filed on Apr. 16, 2004, entitled "BLOOD CLOT FILTER HAVING A COLLAPSED REMEMBERED STATE," the entire contents of which are incorporated herein by reference.

BACKGROUND OF THE INVENTION

The present invention relates to medical devices. More particularly, the invention relates to a removable vena cava clot filter that can be percutaneously placed in and removed from the vena cava of a patient.

Filtering devices that are percutaneously placed in the vena cava have been available for over thirty years. A need for filtering devices arises in trauma patients, orthopedic surgery patients, neurosurgery patients, or in patients having medical conditions requiring bed rest or non-movement. During such medical conditions, the need for filtering devices arises due to the likelihood of thrombosis in the peripheral vasculature of patients wherein thrombi break away from the vessel wall, risking downstream embolism or embolization. For example, depending on the size, such thrombi pose a serious risk of pulmonary embolism wherein blood clots migrate from the peripheral vasculature through the heart and into the lungs.

A filtering device can be deployed in the vena cava of a patient when, for example, anticoagulant therapy is contraindicated or has failed. Typically, filtering devices are permanent implants, each of which remains implanted in the patient for life, even though the condition or medical problem that required the device has passed. In more recent years, filters have been used or considered in preoperative patients and in patients predisposed to thrombosis which places the patient at risk for pulmonary embolism.

The benefits of a vena cava filter have been well established, but improvements may be made. For example, filters generally have not been considered removable from a patient due to the likelihood of endotheliosis of the filter or fibrous reaction matter adherent to the endothelium during treatment. After deployment of a filter in a patient, proliferating intimal cells begin to accumulate around the filter struts which contact the wall of the vessel. After a length of time, such ingrowth prevents removal of the filter without risk of trauma, requiring the filter to remain in the patient. As a result, there has been a need for an effective filter that can be removed after the underlying medical condition has passed.

Moreover, conventional filters commonly become off-centered or tilted with respect to the hub of the filter and the longitudinal axis of the vessel in which it has been inserted. As a result, the filter including the hub and the retrieval hook engage the vessel wall along their lengths and potentially become endothelialized therein. This condition is illustrated in prior art FIG. 1a in which a prior art filter 113 has been delivered by a delivery sheath 125 through the vessel 150 of a patient. In the event of this occurrence, there is a greater likelihood of endotheliosis of the filter to the blood vessel along a substantial length of the filter wire. As a result, the filter becomes a permanent implant in a shorter time period than otherwise.

Furthermore, further improvements may be made related to the delivery or retrieval of vena cava filters. For delivery of vena cava filters, an introducer system having an introducer tube may be percutaneously inserted in the vena cava of a patient through the femoral vein or the jugular vein. A part of an introducer assembly 120 is illustrated in prior art FIG. 1b in which the prior art filter 113 is percutaneously delivered through the jugular vein 154 of a patient. As shown, the filter 113 in its collapsed configuration is placed at the distal end 121 of an inner sheath 122 with anchoring hooks 116 of the filter 113 extending past the distal end 121. An outer sheath 126 is then disposed over the inner sheath 122 to avoid undesirably scratching or scraping of the anchoring hooks 116 against the introducer tube 130. The inner and outer sheaths 122, 126 along with a pusher member 132 are then moved together through the introducer tube 130 to deliver the filter 113 to the vena cava of the patient.

It has been a challenge to design a vena cava filter with features that lessen the concerns of undesirably scratching or scraping of the anchoring hooks against outer walls of an introducer tube or a blood vessel while maintaining the effectiveness of the filter.

BRIEF SUMMARY OF THE INVENTION

One embodiment of the present invention generally provides a removable vena cava filter configured for simplified delivery to and retrieval from the vena cava of a patient. The filter is shaped for improved delivery and retrieval. The filter includes primary struts, each of which having an arcuate segment that extends to an anchoring hook. In a collapsed state, each primary strut is configured to cross another primary strut along a center axis of the filter such that the arcuate segments occupy a first diameter greater than a second diameter occupied by the anchoring hooks. As a result, the arcuate segments widen a path in a vessel when the filter is retrieved. Thus, the filter is able to be retrieved with greater ease and with a reduced likelihood of undesirably scratching or scraping of the anchoring hooks against outer walls of a blood vessel in the collapsed state.

The present invention provides a removable vena cava filter for capturing thrombi in a blood vessel. In one embodiment, the filter comprises a plurality of primary struts having first ends attached together along a longitudinal axis. Each primary strut has an arcuate segment extending from the first end to an anchoring hook. The primary struts are configured to move between an expanded state for engaging the anchoring hooks with the blood vessel and a collapsed state for filter retrieval or delivery. Each primary strut are configured to cross another primary strut along the longitudinal axis in the collapsed state such that the arcuate segments occupy a first diameter greater than a second diameter occupied by the anchoring hooks in the collapsed state for filter retrieval or delivery.

In another embodiment, the filter further comprises a plurality of secondary struts having connected ends attached together along the longitudinal axis and extending therefrom to free ends to centralize the filter in the expanded state in the blood vessel. The filter further comprises a hub configured to axially house the first ends of the plurality of primary struts. The filter further includes a retrieval hook extending from the hub opposite the plurality of primary struts for removal of the filter from the blood vessel.

In yet another embodiment, the present invention provides a removable filter assembly for capturing thrombi in a blood vessel. In this embodiment, the assembly comprises the removable filter and an introducer tube in which the removable filter in the collapsed state is disposed for retrieval or delivery.

In certain embodiments, pairs of secondary struts are positioned between pairs of primary struts. Each pair of secondary struts is twisted together near the connected ends of the secondary struts to form a twisted section. The twisted sections of the secondary struts effectively stiffen the struts to enhance their centering capabilities to prevent the filter from tilting when the filter is deployed in the blood vessel. Hence, engagement between the struts and the blood vessel is minimized which reduces the potential for the struts to become endothelialized within the blood vessel. A further feature of the twisted sections is that they prevent or at least minimize the secondary struts from entangling with the primary struts.

Further aspects, features, and advantages of the invention will become apparent from consideration of the following description and the appended claims when taken in connection with the accompanying drawings.

DETAILED DESCRIPTION OF THE INVENTION

Figure 2:
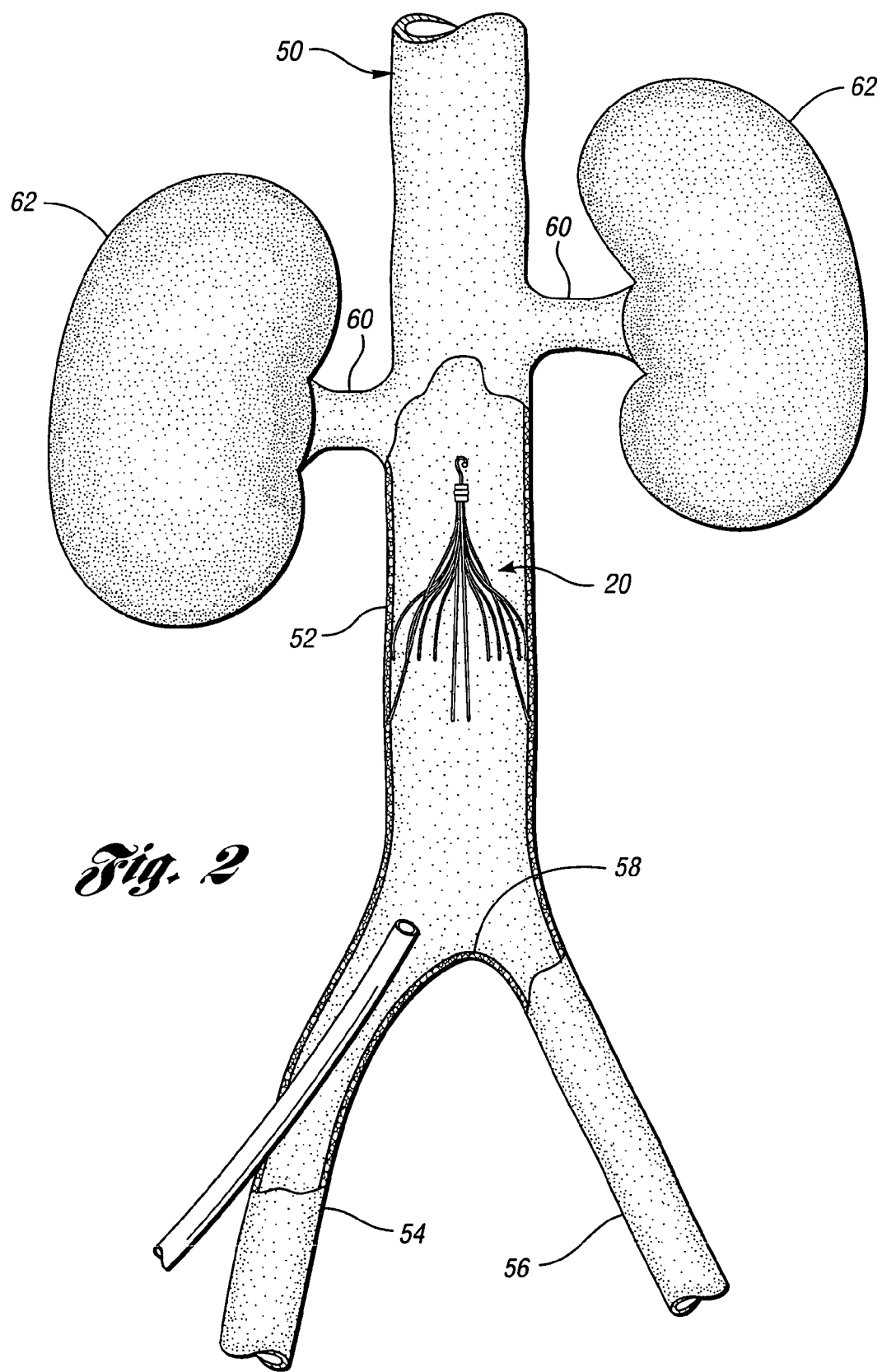
FIG. 2 is an illustration of the anatomy of the renal veins, the iliac veins, and the vena cava in which one embodiment of a vena cava filter of the present invention is deployed.

In accordance with one embodiment of the present invention, FIG. 2 illustrates a vena cava filter 10 implanted in the vena cava 50 for the purpose of lysing or capturing thrombi carried by the blood flowing through the iliac veins 54, 56 toward the heart and into the pulmonary arteries. As shown, the iliac veins merge at juncture 58 into the vena cava 50. The renal veins 60 from the kidneys 62 join the vena cava 50 downstream of juncture 58. The portion of the vena cava 50, between the juncture 58 and the renal veins 60, defines the inferior vena cava 52 in which the vena cava filter 10 has been percutaneously deployed through the femoral veins. Preferably, the vena cava filter 10 has a length smaller than the length of the inferior vena cava 52. If the lower part of the filter extends into the iliac veins, filtering effectiveness will be compromised and if the filter wires cross over the origin of the renal veins the filter wires might interfere with the flow of blood from the kidneys.

Figure 3A:
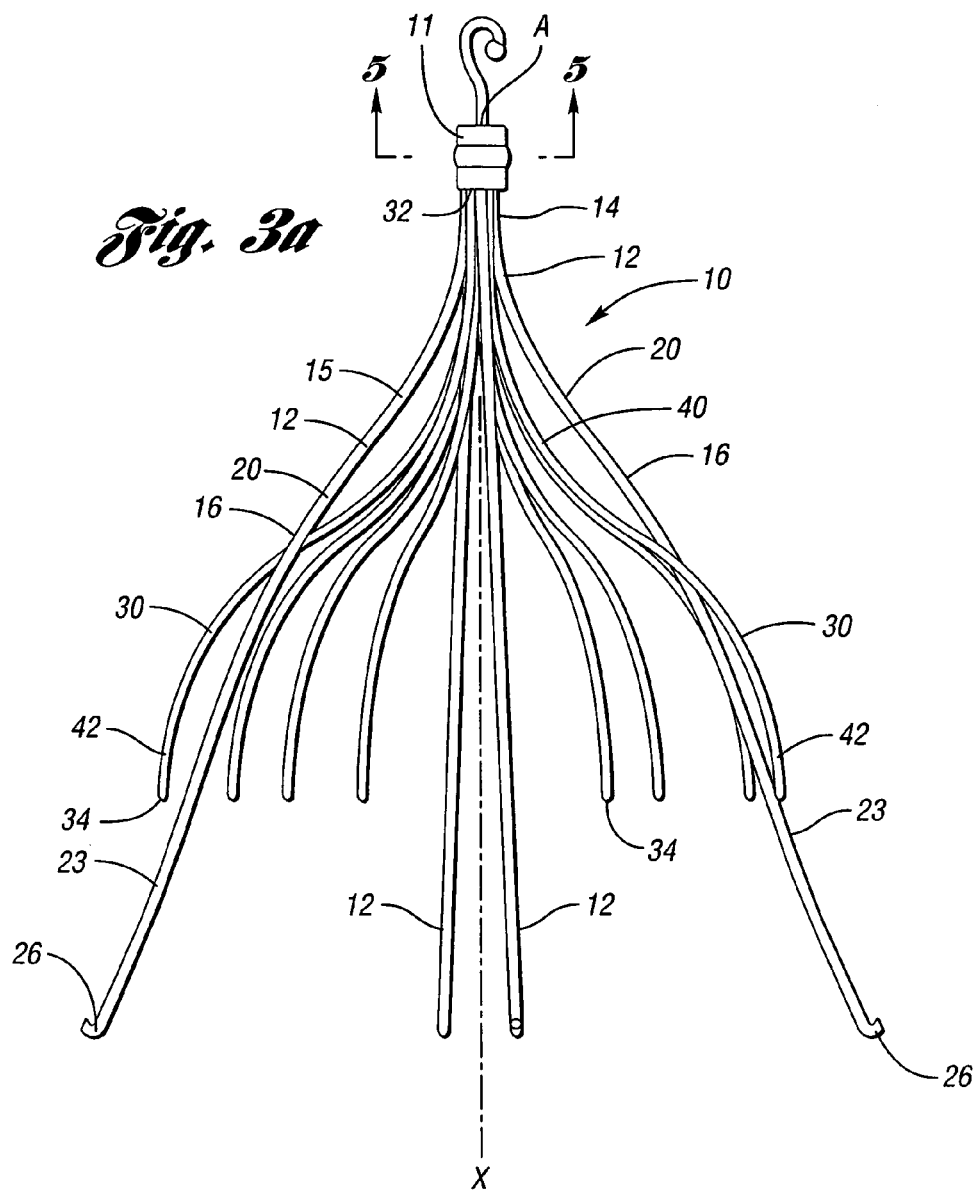
FIG. 3a is a side perspective view of one embodiment of the vena cava filter in an expanded state.

This embodiment of the present invention will be further discussed with reference to FIGS. 3-9 in which filter 10 is shown. FIG. 3a illustrates filter 10 in an expanded state and comprising four primary struts 12 each having first ends that emanate from a hub 11. Hub 11 attaches by crimping first ends 14 of primary struts 12 together at a center point A in a compact bundle along a central or longitudinal axis X of the filter. The hub 11 has a minimal diameter for the size of wire used to form the struts. Preferably, the primary struts 12 are formed from a superelastic material, stainless steel wire, Nitinol, cobalt-chromium-nickel-molybdenum-iron alloy, or cobalt chrome-alloy, or any other suitable material that will result in a self-opening or self-expanding filter. In this embodiment, the primary struts 12 are preferably formed from wire having a round cross-section with a diameter of at least about 0.015 inches. Of course, it is not necessary that the primary struts have a round or near round cross-section. For example, the primary struts 12 could take on any shape with rounded edges to maintain non-turbulent blood flow therethrough.

Each primary strut 12 includes an arcuate segment 16 having a soft S-shape. Each arcuate segment 16 is formed with a first curved portion 20 that is configured to softly bend away from the longitudinal or central axis X of the filter 10 and a second curved portion 23 that is configured to softly bend toward the longitudinal axis of the filter 10. Due to the soft bends of each arcuate segment 16, a prominence or a point of inflection on the primary strut 12 is substantially avoided to aid in non-traumatically engaging the vessel wall.

Figures 8A, 8B:
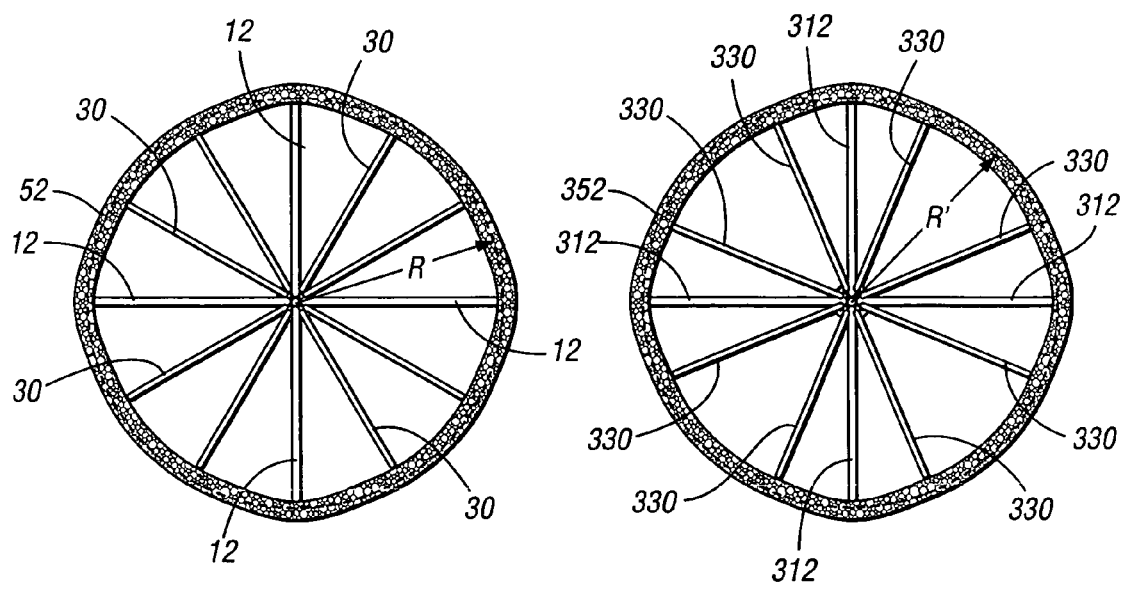
FIG. 8a is a cross-sectional view of the vena cava of FIG. 7a taken along line 8-8.
FIG. 8b is a cross-sectional view of the vena cava of FIG. 7a taken along line 8-8 depicting another embodiment of the filter.

The primary struts 12 terminate at anchoring hooks 26 that will anchor in the vessel wall when the filter 10 is deployed at a delivery location in the blood vessel. The primary struts 12 are configured to move between an expanded state for engaging the anchoring hooks 26 with the blood vessel and a collapsed state or configuration for filter retrieval or delivery. In the expanded state, each arcuate segment 16 extends arcuately along a longitudinal axis X (as shown in FIG. 3a) and linearly relative to a radial axis R (as shown in FIG. 8a) from the first end 14 to the anchoring hook 26. As shown in FIG. 8a, the primary struts 12 radially extend from the first ends 14, defining the radial axis R. In this embodiment, the primary struts 12 extend linearly relative to the radial axis R and avoid entanglement with other struts.

As discussed in greater detail below, the soft bends of each arcuate segment 16 allow each primary strut 12 to cross another primary strut 12 along the longitudinal axis X in the collapsed state such that each anchoring hook 26 faces the longitudinal axis X for filter retrieval or delivery.

When the filter 10 is deployed in a blood vessel, the anchoring hooks 26 engage the walls of the blood vessel to define a first axial portion to secure the filter in the blood vessel. The anchoring hooks 26 prevent the filter 10 from migrating from the delivery location in the blood vessel where it has been deposited. The primary struts 12 are shaped and dimensioned such that, when the filter 10 is freely expanded, the filter 10 has a diameter of between about 25 mm and 45 mm and a length of between about 3 cm and 7 cm. For example, the filter 10 may have a diameter of about 35 mm and a length of about 5 cm. The primary struts 12 have sufficient spring strength that when the filter is deployed the anchoring hooks 26 will anchor into the vessel wall.

In this embodiment, the filter 10 includes a plurality of secondary struts 30 having connected ends 32 that also emanate from hub 11. Hub 11 attaches the connected ends 32 by crimping at the center point A of the secondary struts 30 together with the primary struts 12. In this embodiment, each primary strut 12 has two secondary struts 30 in side-by-side relationship with the primary strut 12. The secondary struts 30 extend from the connected ends 32 to free ends 34 to centralize the filter 10 in the expanded state in the blood vessel. As shown, each secondary strut 30 extends arcuately along the longitudinal axis and linearly relative to the radial axis from the connected end 32 to the free end 34 for engaging the anchoring hooks 26 with the blood vessel. As with the primary struts 12, the secondary struts 30 extend linearly relative to the radial axis and avoid entanglement with other struts.

The secondary struts 30 may be made from the same type of material as the primary struts 12. However, the secondary struts 30 may have a smaller diameter, e.g., at least about 0.012 inches, than the primary struts 12. In this embodiment, each of the secondary struts 30 is formed of a first arc 40 and a second arc 42. The first arc 40 extends from the connected end 32 away from the longitudinal axis X. The second arc 42 extends from the first arc 40 towards the longitudinal axis X. As shown, two secondary struts 30 are located on each side of one primary strut 12 to form a part of a netting configuration of the filter 10. The hub 11 is preferably made of the same material as the primary struts and secondary struts to minimize the possibility of galvanic corrosion or molecular changes in the material due to welding.

When freely expanded, free ends 34 of the secondary struts 30 will expand radially outwardly to a diameter of about 25 mm to 45 mm to engage the vessel wall. For example, the secondary struts 30 may expand radially outwardly to a diameter of between about 35 mm and 45 mm. The second arcs 42 of the free ends 34 engage the wall of a blood vessel to define a second axial portion where the vessel wall is engaged. The secondary struts 30 function to stabilize the position of the filter 10 about the center of the blood vessel in which it is deployed. As a result, the filter 10 has two layers or portions of struts longitudinally engaging the vessel wall of the blood vessel. The length of the filter 10 is preferably defined by the length of a primary strut 12.

Furthermore, the diameter of the hub 11 is defined by the size of a bundle containing the primary struts 12 and secondary struts 30. In this embodiment, the eight secondary struts 30 minimally add to the diameter of the hub 11 or the overall length of the filter 10, due to the reduced diameter of each secondary strut 30. This is accomplished while maintaining the filter 10 in a centered attitude relative to the vessel wall and formed as a part of the netting configuration of the filter 10. As shown, removal hook 46 extends from hub 11 opposite primary and secondary struts 12 and 30.

In this embodiment, each arcuate segment 16 has a thickness of at least about 0.015 inch and a tensile strength of between about 285,000 pounds per square inch (psi) and 330,000 psi. Each anchoring hook 26 is integral with the arcuate segment 16 and has the thickness and the tensile strength of the arcuate segment. Each secondary strut 30 has a thickness of at least about 0.012 inch and a tensile strength of between about 285,000 psi and 330,000 psi.

Figure 1:
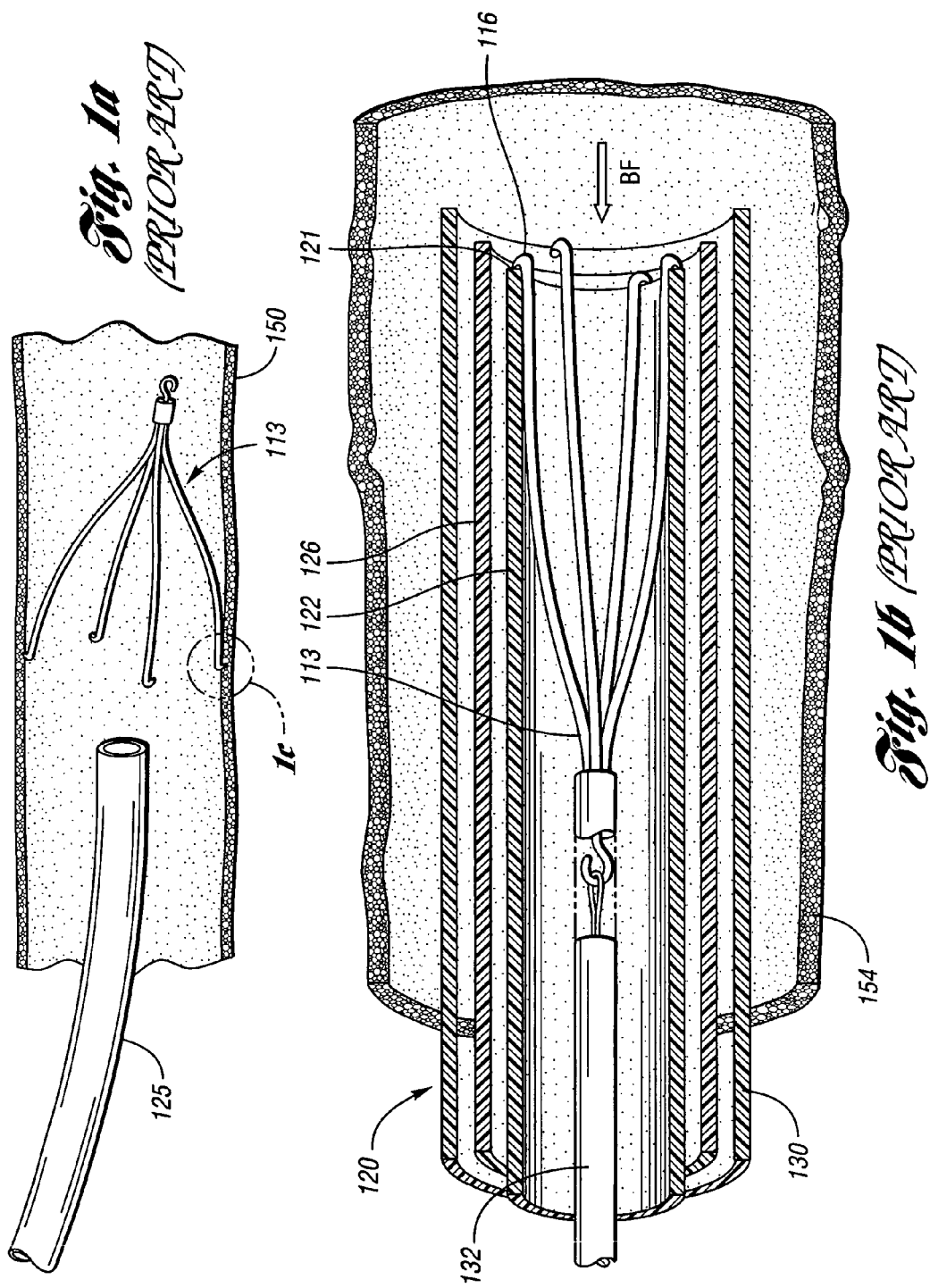
FIG. 1a is a side view of a prior art filter deployed through the vasculature of a patient.
FIG. 1b is a side view of an introducer assembly including the prior art filter to be delivered to the vena cava of a patient.
Figure 3B:
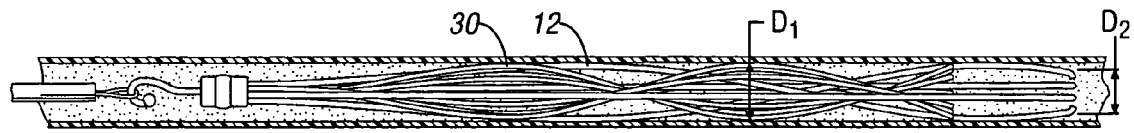
FIG. 3b is a side view of the vena cava filter of FIG. 3a in a collapsed state and disposed in an introducer tube.

FIG. 3b illustrates the filter 10 in a collapsed state disposed in a delivery/retrieval tube 94 for delivery or retrieval. As shown, the filter 10 is shaped for each primary strut 12 to cross another primary strut 12 along the longitudinal axis X. As a result, in the collapsed state, the anchoring hooks 26 are configured to invert or inwardly face the longitudinal axis X for retrieval and delivery of the filter 10. This inverted or inwardly facing configuration of the anchoring hooks 26 allows for simplified delivery and retrieval of filter 10. For example, a concern that the anchoring hooks 26 may scrape, scratch, or tear the inner wall of a delivery/retrieval tube is eliminated, since the filter 10 of the present invention is shaped to have the anchoring hooks 26 face each other in the collapsed state. In fact, a set of inner and outer delivery/retrieval sheaths (see prior art FIG. 1b) may be eliminated during the delivery or retrieval of the filter 10 through the jugular or femoral vein. Rather, merely one delivery/retrieval tube with a loop snare mechanism may be used to deliver or retrieve the filter 10 of the present invention.

In the collapsed state, each primary strut 12 is configured to cross another primary strut 12 along the longitudinal axis X such that the arcuate segments 16, first curved portions 20 or second curved portions 23, occupy a first diameter $D_1$. In this embodiment, the first diameter is greater than a second diameter $D_2$ occupied by the anchoring hooks 26 for filter retrieval or delivery. It has been found that the first diameter of the arcuate segments 16 serves to clear a path of retrieval, reducing radial force from the sheath or blood vessel on the anchoring hooks 26 during removal of the filter 10 from a patient. Reducing the radial force on the anchoring hooks 26 assists in preventing the anchoring hooks 26 from scraping, scratching, or tearing the inner wall of a sheath during removal of the filter 10 from a patient.

In this embodiment of the present invention, it is to be noted that the filter 10 may be delivered or retrieved by any suitable introducer (delivery or retrieval) tube. However, it is preferred that the introducer tube has an inside diameter of between about 4.5 French and 16 French, and more preferably between about 6.5 French and 14 French. Thus, the collapsed state of the filter may be defined by the inside diameter of an introducer tube.

Figure 4:
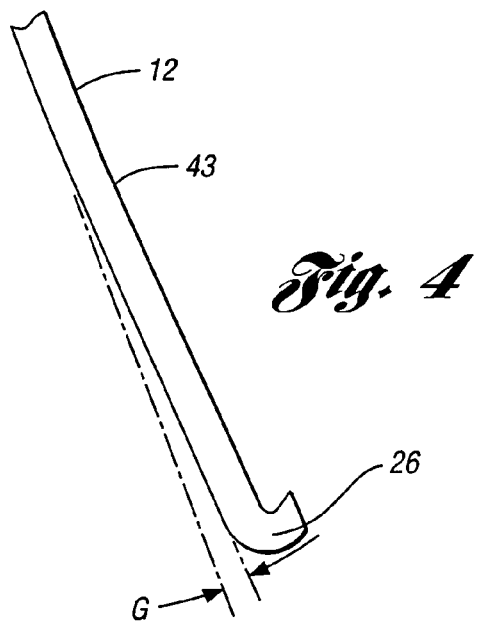
FIG. 4 is an enlarged view of a portion of a second arcuate portion of a primary strut of the vena cava filter.

FIG. 4 illustrates primary strut 12 including distal bend 43 formed thereon and extending outwardly radially from the longitudinal axis X. As shown in FIG. 4, the distal bend 43 may extend outwardly at an angle between about 0.5 degree to 2 degrees, preferably 1.0 degree. The distal bend 43 allows the filter 10 to filter thrombi effectively at a smaller inside diameter of a blood vessel than otherwise would be possible while maintaining the ability to collapse for delivery or retrieval.

Figure 5:
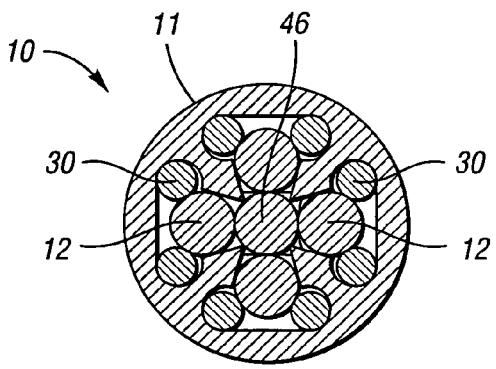
FIG. 5 is a cross-sectional view of a hub of the filter in FIG. 3 taken along line 5-5.

FIG. 5 illustrates a cross-sectional view of the filter 10 of FIG. 3a at hub 11. As shown, the hub 11 houses a bundle of first ends 14 of the four primary struts 14 and connected ends 32 of secondary struts 30. FIG. 5 further depicts the configurations of the primary and secondary struts 12 and 30. In this embodiment, the primary struts 12 are spaced between two secondary struts 30. Of course, the primary struts 12 may be spaced between any other suitably desired number of secondary struts 30 without falling beyond the scope or spirit of the present invention.

Figure 6A:
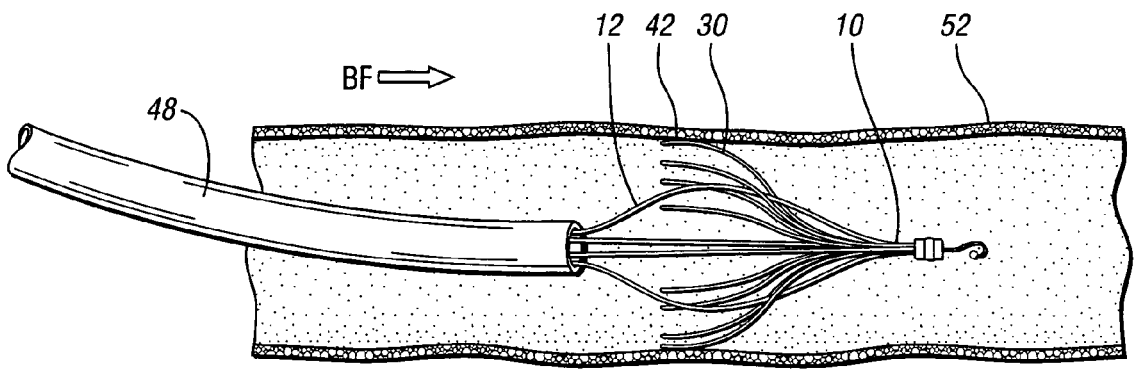
FIG. 6a is a cross-sectional view of the vena cava depicting the filter partially deployed leading with the removal hook.
Figure 6B:
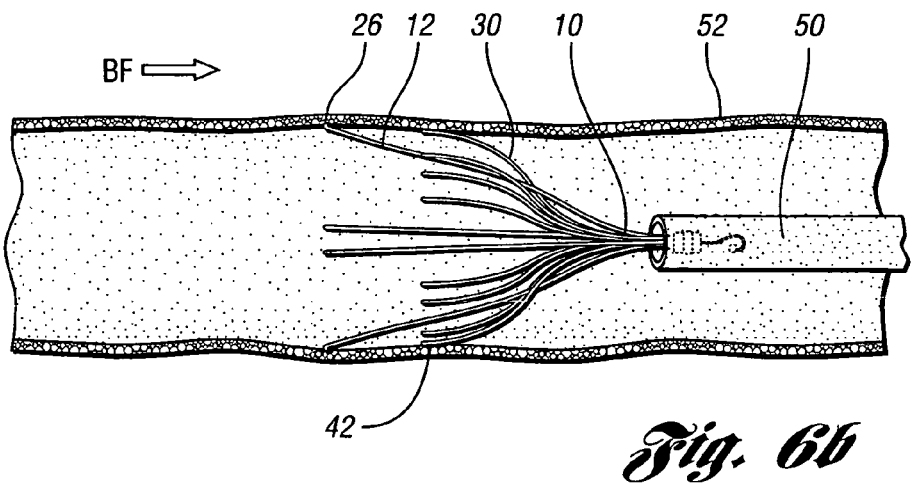
FIG. 6b is a cross-sectional view of the vena cava depicting the filter partially deployed leading with the anchoring hooks.

In this embodiment, FIGS. 6a and 6b both illustrate the filter 10 partially deployed in inferior vena cava 52. FIG. 6a shows the filter 10 being delivered by a delivery tube 48 through the femoral vein of a patient and FIG. 6b shows the filter 10 being delivered by a delivery tube 50 through the jugular vein of a patient. For deployment of the filter 10, a delivery tube is percutaneously inserted through the patient's vessel such that the distal end of the delivery tube is at the location of deployment. In this embodiment, a wire guide is preferably used to guide the delivery tube to the location of deployment. In FIG. 6a, the filter 10 is inserted through the proximal end of the delivery tube 48 with the removal hook 46 leading and anchoring hooks 26 of the primary struts 12 held by a filter retainer member for delivery via the femoral vein of a patient.

In FIG. 6b, the filter 10 is inserted through the proximal end of the delivery tube 50 with the anchoring hooks 26 of the primary struts 12 leading and the removal hook 46 trailing for delivery via the jugular vein of a patient. In this embodiment, a pusher wire having a pusher member at its distal end may be fed through the proximal end of the delivery tube 50 thereby pushing the filter 10 until the filter 10 reaches the distal end of the delivery tube 50 to a desired location.

During deployment, the secondary struts 30 expand first to centralize or balance the filter within the vessel. When the free ends of the secondary struts emerge from the distal end of either of the delivery tubes 48 or 50, the secondary struts 30 expand to an expanded position as shown in both FIGS. 6a and 6b. The second arcs 42 engage the inner wall of the vessel. The second arcs 42 of the secondary struts 30 function to stabilize the attitude of filter 10 about the center of the blood vessel. When delivering through the jugular vein (FIG. 6b), the filter 10 is then pushed further by the pusher wire (not shown) until it is fully deployed.

When the filter 10 is fully expanded in the vena cava, the anchoring hooks 26 of the primary struts 12 and the second arcs 42 of the secondary struts 30 are in engagement with the vessel wall. The anchoring hooks 26 of the primary struts 12 have anchored the filter 10 at the location of deployment in the vessel, preventing the filter 10 from moving with the blood flow through the vessel. As a result, the filter 10 is supported by two sets of struts that are spaced axially along the length of the filter.

Figure 7:
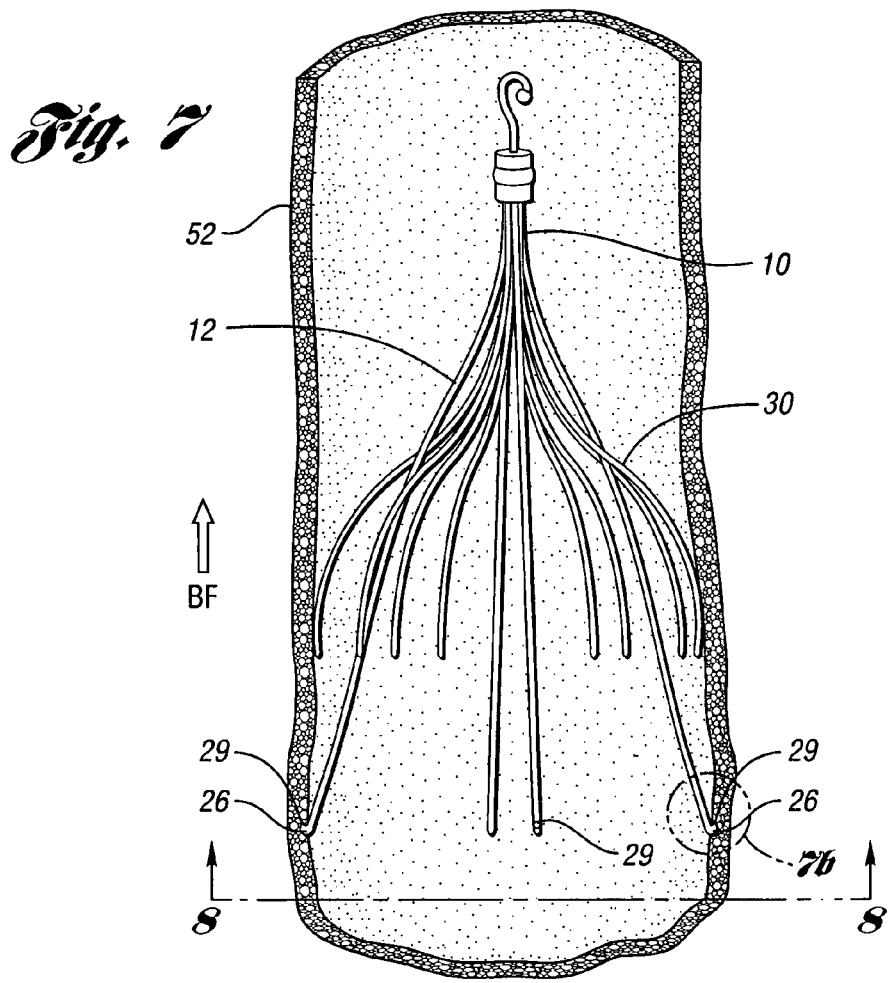
FIG. 7 is a cross-sectional view of the vena cava in which the filter of FIG. 3 has been deployed.

FIG. 7 illustrates the filter 10 fully expanded after being deployed in inferior vena cava 52. As shown, the inferior vena cava 52 has been broken away so that the filter 10 can be seen. The direction of the blood flow BF is indicated in FIG. 7 by the arrow that is labeled BF. The anchoring hooks 26 at the ends of the primary struts 12 are shown as being anchored in the inner lining of the inferior vena cava 52. The anchoring hooks 26 include barbs 29 that, in one embodiment, project toward the hub 11 of the filter. The barbs 29 function to retain the filter 10 in the location of deployment.

The spring biased configuration of the primary struts 12 further causes the anchoring hooks 26 to engage the vessel wall and anchor the filter at the location of deployment. After initial deployment, the pressure of the blood flow on the filter 10 contributes in maintaining the barbs 29 anchored in the inner lining of the inferior vena cava 52. As seen in FIG. 7, the second arcs 42 of secondary struts 30 also have a spring biased configuration to engage with the vessel wall.

As seen in FIG. 7, the hub 11 and removal hook 46 are positioned downstream from the location at which the anchoring hooks 26 are anchored in the vessel. When captured by the struts 12 and 30, thrombi remains lodged in the filter. The filter 10 along with the thrombi may then be percutaneously removed from the vena cava. When the filter 10 is to be removed, the removal hook 46 is preferably grasped by a retrieval instrument that is percutaneously introduced in the vena cava in the direction of removal hook 16 first.

FIG. 8a depicts a netting configuration or pattern formed by the primary struts 12, secondary struts 30, and the hub 11 relative to radial axis R. The netting pattern shown in FIG. 8a functions to catch thrombi carried in the blood stream prior to reaching the heart and lungs to prevent the possibility of a pulmonary embolism. The netting pattern is sized to catch and stop thrombi that are of a size that are undesirable to be carried in the vasculature of the patient. Due to its compacted size, the hub minimally resists blood flow.

FIG. 8a depicts the netting pattern including primary struts and secondary struts at substantially equal angular space relative to each other. The netting pattern provides an even distribution between the primary and secondary struts to the blood flow, increasing the likelihood of capturing thrombi. However, as shown in FIG. 8b, it is to be understood that each of the sets of primary struts 312 and secondary struts 330 may be independently spaced substantially equally at their respective portions relative to radial axis R'. For example, the secondary struts 330 may be spaced equally relative to the other secondary struts 330 and the primary struts 312 may be spaced equally relative to the other primary struts 312. As a result, the netting pattern in this embodiment shown by the cross-sectional view of the vena cava (taken along line 8-8) will have uneven or unequal spacing between the primary struts 312 and secondary struts 330.

Figure 9A:
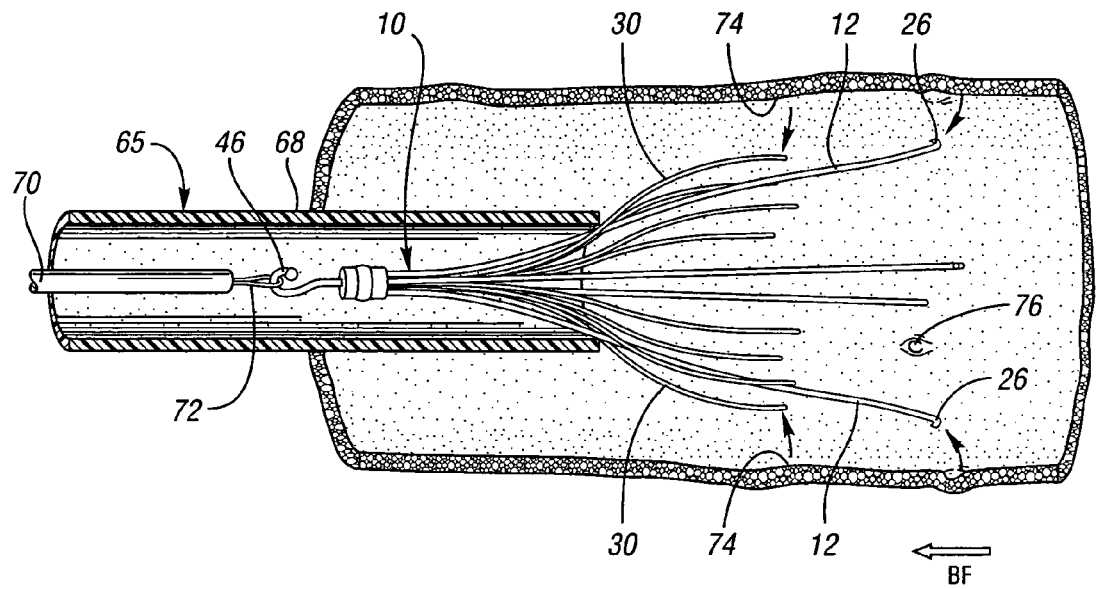
FIG. 9a is a cross-sectional view of a blood vessel in which a retrieval sheath engages primary struts of the filter in FIG. 3 for removal.
Figure 9B:
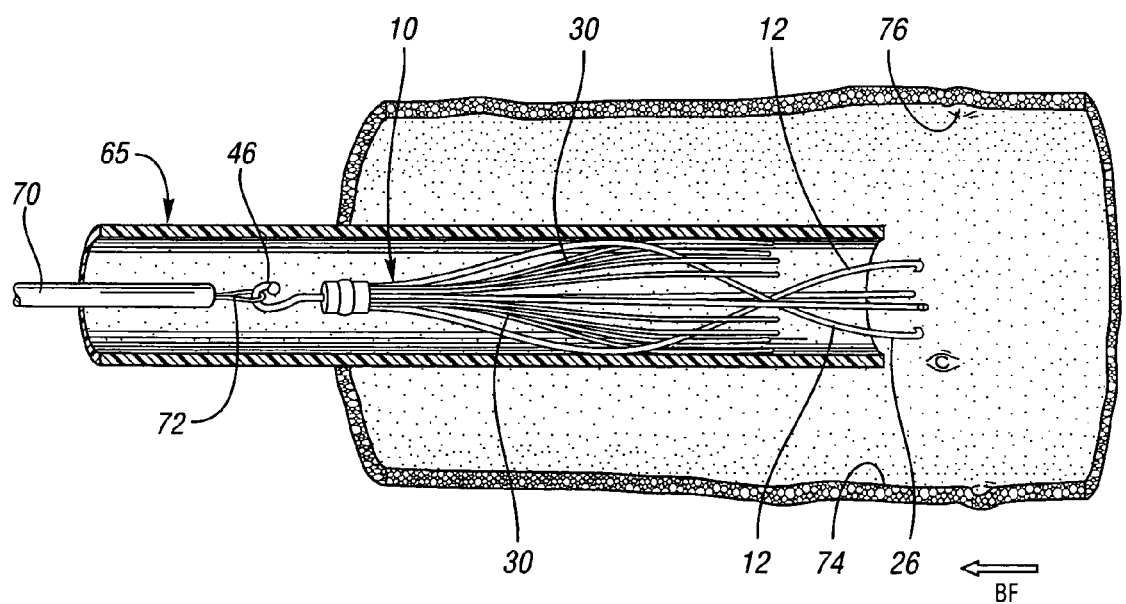
FIG. 9b is a cross-sectional view of a blood vessel in which the retrieval sheath includes the filter in the collapsed state for removal.

FIG. 9a illustrates part of a retrieval device 65 being used in a procedure for removing the filter 10 from the inferior vena cava 52. In this example, the retrieval device 65 is percutaneously introduced into the superior vena cava via the jugular vein. In this procedure, a removal catheter or sheath 68 of the retrieval device 65 is inserted into the superior vena cava. A wire 70 having a loop snare 72 at its distal end is threaded through the removal sheath 68 and is exited through the distal end of the sheath 68. The wire 70 is then manipulated by any suitable means from the proximal end of the retrieval device such that the loop snare 72 captures the removal hook 46 of the filter 10. Using counter traction by pulling the wire 70 while pushing the sheath 68, the sheath 68 is passed over the filter 10. As the sheath 68 passes over the filter 10, the primary struts 12 and then the secondary struts 30 engage the edge of the sheath 68 and are caused to pivot or undergo bend deflection at the hub 11 toward the longitudinal axis of the filter. The pivoting toward the longitudinal axis causes the ends of the struts 12 and 30 to be retracted from the vessel wall. In this way, only surface lesions 74 and small point lesions 76 on the vessel wall are created in the removal procedure. As shown, the surface lesions 74 are created by the ends of the secondary struts 30 and the small point legions 76 are created by the anchoring hooks 26 of the primary struts 12. However, it is to be noted that any other suitable procedure may be implemented to remove the filter from the patient.

Although the embodiments of this device have been disclosed as preferably being constructed from wire having a round cross section, it could also be cut from a tube of suitable material by laser cutting, electrical discharge machining or any other suitable process.

The primary and secondary struts can be formed from any suitable material that will result in a self-opening or self-expanding filter, such as shape memory alloys. Shape memory alloys have the desirable property of becoming rigid, that is, returning to a remembered state, when heated above a transition temperature. A shape memory alloy suitable for the present invention is Ni—Ti available under the more commonly known name Nitinol. When this material is heated above the transition temperature, the material undergoes a phase transformation from martensite to austenite, such that material returns to its remembered state. The transition temperature is dependent on the relative proportions of the alloying elements Ni and Ti and the optional inclusion of alloying additives.

In other embodiments, both the primary struts and the secondary struts are made from Nitinol with a transition temperature that is slightly below normal body temperature of humans, which is about 98.6° F. Thus, when the filter is deployed in the vena cave and exposed to normal body temperature, the alloy of the struts will transform to austenite, that is, the remembered state, which for the present invention is an expanded configuration when the filter is deployed in the blood vessel. To remove the filter, the filter is cooled to transform the material to martensite which is more ductile than austenite, making the struts more malleable. As such, the filter can be more easily collapsed and pulled into the sheath for removal.

In certain embodiments, both the primary struts and the secondary struts are made from Nitinol with a transition temperature that is above normal body temperature of humans, which is about 98.6° F. Thus, when the filter is deployed in the vena cave and exposed to normal body temperature, the struts are in the martensitic state so that the struts are sufficiently ductile to bend or form into a desired shape, which for the present invention is an expanded configuration. To remove the filter, the filter is heated to transform the alloy to austenite so that the filter becomes rigid and returns to a remembered state, which for the filter is a collapsed configuration.

Figure 10:
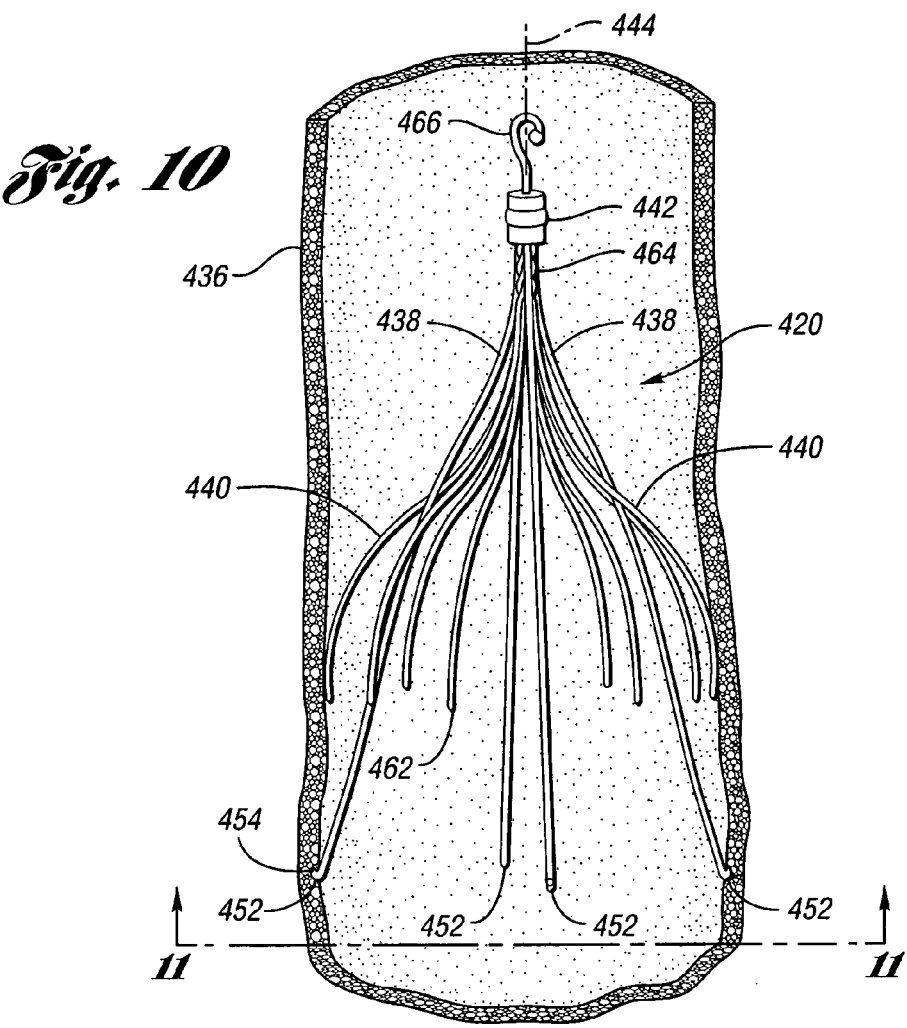
FIG. 10 is a cross-sectional view of a blood vessel showing a vena cava filter deployed within the blood vessel in accordance with another embodiment of the invention.
Figure 11:
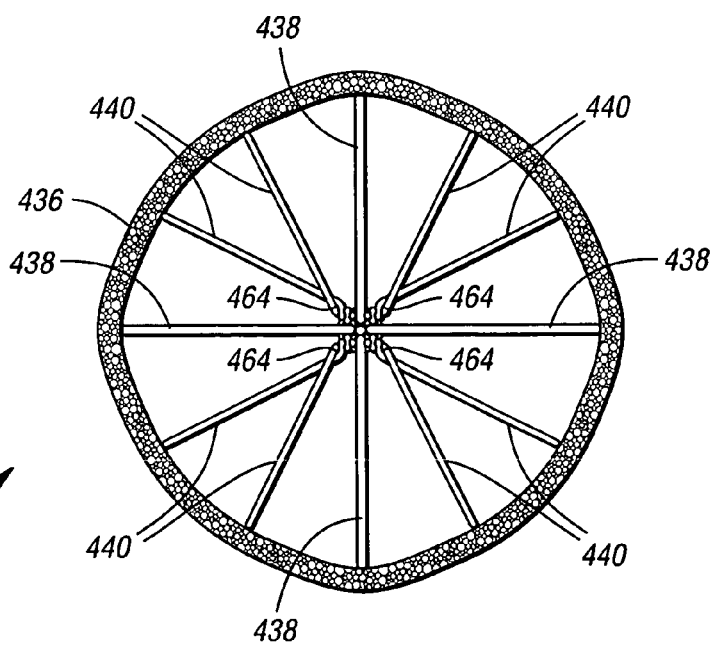
FIG. 11 is a view of the blood vessel and filter of FIG. 10 taken along the line 11-11.

In another embodiment shown in FIGS. 10 and 11, a filter 420 includes four primary struts 438 and eight secondary struts 440 that extend from a hub 442. Each primary strut 438 terminates in an anchoring hook 452 with a barb 454. The primary struts 438 have sufficient spring strength such that when the filter is deployed in a vena cava 436, the anchoring hooks 452, in particular, the barbs 444, anchor into the vessel wall of the vena cava 436 to prevent the filter 420 from migrating from the delivery location. The pressure of the blood flow on the filter 420 contributes in maintaining the barbs 454 anchored in the inner lining of the vena cava 436.

A pair of secondary struts 440 are positioned between adjacent primary struts 438. Each secondary strut 440 extends from the hub 442 and terminates in a tip 462 pointing toward the central axis 444. The tips 462 are located longitudinally between the hub 442 and the anchoring hooks 454 of the primary struts 438. The connected ends of each pair of secondary struts 440 positioned between adjacent primary struts are twisted together, defining a twisted section 464.

Since the twisted sections 464 effectively stiffens each pair of secondary struts 440, thinner secondary struts may be used to provide the appropriate balancing forces to center the filter in the blood vessel. Moreover, an additional benefit of the twisted section is that they prevent the secondary struts from entangling with the primary struts.

The secondary struts 440 can be made from the same type of material as the primary struts 438 and can be formed by the same process used to form the primary struts. However, the secondary struts may have a smaller diameter than the primary struts. To form the twisted sections 464, each pair of secondary struts 440 positioned between adjacent primary struts 438 can be twisted about each other after the struts have been attached to the hub 442. Each twisted section 464 includes one or more twists. For example, each twisted section 464 may include up to about ten twists. In certain implementations, the number of twists in each section 464 may be between about three to five twists. Increasing the number of twists increases the stiffness of the pair of secondary struts twisted about each other. The hub 442 is preferably made of the same material as the primary struts and secondary struts to minimize the possibility of galvanic corrosion.

FIG. 11 illustrates a netting pattern ("net") formed by the primary struts 438, the secondary struts 440, and the hub 442. This net functions to catch thrombi carried in the blood stream to prevent the thrombi from reaching the heart and lungs, where the thrombi could cause pulmonary embolism. The net is sized to catch and stop thrombi that are of a size that are undesirable in the vasculature of the patient. As illustrated, the struts 438 have substantially equal angular spacing between the struts.

The hub 442 and a removal hook 466 attached to the hub are located downstream of the location at which the anchoring hooks 452 are anchored in the vessel 436. When captured by the struts, thrombi remain lodged in the filter 420. The filter 420 along with the thrombi may then be removed percutaneously from the vena cava. When the filter 420 is to be removed, the removal hook 466 is typically grasped by the retrieval hook that is introduced in the vena cava percutaneously.

While the present invention has been described in terms of preferred embodiments, it will be understood, of course, that the invention is not limited thereto since modifications may be made to those skilled in the art, particularly in light of the foregoing teachings.

What we claim is:

1. A removable filter for capturing thrombi in a blood vessel, the filter comprising:
   a plurality of primary struts each having a first length, the primary struts having first ends attached together along a longitudinal axis and housed within a hub, wherein the primary struts emanate from a first end of the hub, each primary strut having an arcuate segment including a first curved portion extending from the first end and a second curved portion extending from the first curved portion and terminating at an anchoring hook, the first and second curved portions defining a soft-S shape, each primary strut extending arcuately along the longitudinal axis and linearly radially, the primary struts being configured to move between an expanded state for engaging the anchoring hooks with the blood vessel and a collapsed state for filter retrieval or delivery, each primary strut being configured to cross another primary strut along the longitudinal axis in the collapsed state such that the arcuate segments occupy a first diameter, the first diameter being the distance between opposite arcuate segments of the primary struts in the collapsed state, the first diameter being greater than a second diameter occupied by the anchoring hooks in the collapsed state for filter retrieval or delivery, the second diameter being the largest diameter occupied by the anchoring hooks in the collapsed state, each primary strut of the plurality of primary struts having a spring biased configuration that is self-expanding; and
   a plurality of secondary struts separate from the primary struts, the secondary struts having a second length and connected ends attached together along the longitudinal axis and housed within the hub, wherein the secondary struts emanate from the first end of the hub and extend arcuately therefrom to free ends to centralize the filter in the expanded state in the blood vessel, each secondary strut extending arcuately along the longitudinal axis and linearly radially, each secondary strut having a first arc extending from the connected end away from the longitudinal axis and a second arc extending from the first arc towards the longitudinal axis, the second arc extending to the free end without a hook, the secondary struts having a smaller diameter than the primary struts, wherein the length of the filter is defined by the first length of the primary struts.

2. The removable filter of claim 1 further comprising:
a retrieval hook extending from the hub opposite the plurality of primary and secondary struts for removal of the filter from the blood vessel.

3. The removable filter of claim 1 wherein the first curved portion of each primary strut is configured to extend radially from the longitudinal axis of the filter and the second curved portion of each primary struts is configured to extend radially toward the longitudinal axis of the filter.

4. The removable filter of claim 1 wherein each primary strut is formed of a superelastic material, stainless steel wire, Nitinol, cobalt-chromium-nickel-molybdenum-iron alloy, or cobalt-chrome alloy.

5. The removable filter of claim 1 wherein each secondary strut is formed of a superelastic material, stainless steel wire, Nitinol, cobalt-chromium-nickel-molybdenum-iron alloy, or cobalt-chrome alloy.

6. The removable filter of claim 1 wherein the first diameter ranges between about 6 French and 14 French, and the second diameter ranges between about 3 French and 9 French.

7. The removable filter of claim 1 wherein the struts are formed of shape memory alloy with a transition temperature.

8. The removable filter of claim 7 wherein the struts collapse to the collapsed state when the temperature of the struts is about equal to or greater than the transition temperature.

9. The removable filter of claim 7 wherein the struts expand to the expanded state when the temperature of the struts is about equal to or greater than the transition temperature.

10. The filter of claim 1 wherein pairs of secondary struts are positioned between pairs of primary struts, each pair of secondary struts being twisted about each other near the connected ends of the respective secondary struts to form a twisted section.

11. The filter of claim 10 wherein each twisted section includes between about one and ten twists.

12. A removable filter assembly for capturing thrombi in a blood vessel, the assembly comprising:
a removable filter comprising:
a plurality of primary struts each having a first length, the primary struts having first ends attached together along a longitudinal axis and housed within a hub, wherein the primary struts emanate from a first end of the hub, each primary strut having an arcuate segment including a first curved portion extending from the first end and a second curved portion extending from the first curved portion and terminating at an anchoring hook, the first and second curved portions defining a soft S-shape, each primary strut extending arcuately along the longitudinal axis and linearly radially, the primary struts being configured to move between an expanded state for engaging the anchoring hooks with the blood vessel and a collapsed state for filter retrieval or delivery, each primary strut being configured to cross another primary strut along the longitudinal axis in the collapsed state such that the arcuate segments occupy a first diameter, the first diameter being the distance between opposite arcuate segments of the primary struts in the collapsed state, and the anchoring hooks occupy a second diameter, the second diameter being the largest diameter occupied by the anchoring hooks in the collapsed state for filter retrieval or delivery, the first diameter being larger than the second diameter, each primary strut of the plurality of primary struts having a spring biased configuration that is self-expanding;
a plurality of secondary struts separate from the primary struts, the secondary struts having a second length and connected ends attached together along the longitudinal axis and housed within the hub, wherein the secondary struts emanate from the first end of the hub and extend therefrom to free ends to centralize the filter in the expanded state in the blood vessel, each secondary strut extending arcuately along the longitudinal axis and linearly radially, each secondary strut having a first arc extending from the connected end away from the longitudinal axis and a second arc extending from the first arc towards the longitudinal axis, the second arc extending to the free end without a hook, the secondary struts having a smaller diameter than the primary struts, wherein the length of the filter is defined by the first length of the primary struts;
a retrieval hook extending from the hub opposite the plurality of primary and secondary struts for removal of the filter from the blood vessel; and
an introducer tube in which the removable filter in the collapsed state is disposed for retrieval or delivery of the filter.

13. The removable filter of claim 12 wherein the first curved portion of each primary strut is configured to extend radially from the longitudinal axis of the filter and the second curved portion of each primary strut is configured to extend radially toward the longitudinal axis of the filter.

14. The removable filter of claim 12 wherein the primary and secondary struts are formed of shape memory alloy with a transition temperature.

15. The removable filter of claim 14 wherein the primary and secondary struts collapse to the collapsed state when the temperature of the primary and secondary struts is about equal to or greater than the transition temperature.

16. The removable filter of claim 14 wherein the primary and secondary struts expand to the expanded state when the temperature of the primary and secondary struts is about equal to or greater than the transition temperature.

17. The removable filter of claim 12 wherein the first diameter ranges between about 6 French and 14 French, and the second diameter ranges between about 3 French and 9 French.

18. A removable filter assembly for capturing thrombi in a blood vessel, the assembly comprising:
a removable filter comprising:
a plurality of primary struts each having a first length, the primary struts having first ends attached together along a longitudinal axis and housed within a hub, wherein the primary struts emanate from a first end of the hub, each primary strut having an arcuate segment including a first curved portion extending from the first end and a second curved portion extending from the first curved portion and terminating at an anchoring hook, the first and second curved portions defining a soft S-shape, each primary strut extending arcuately along the longitudinal axis and linearly radially, the primary struts being configured to move between an expanded state for engaging the anchoring hooks with the blood vessel and a collapsed state for filter retrieval or delivery, each primary strut being configured to cross another primary strut along the longitudinal axis in the collapsed state such that the arcuate segments occupy a first diameter, the first diameter being the distance between opposite arcuate segments of the primary struts in the collapsed state, and the anchoring hooks occupy a second diameter, the second diameter being the largest diameter occupied by the anchoring hooks in the collapsed state for filter retrieval or delivery, the first diameter being larger than the second diameter, each primary strut of the plurality of primary struts having a spring biased configuration that is self-expanding;

a plurality of secondary struts separate from the primary struts, the secondary struts having a second length and connected ends attached together along the longitudinal axis and housed within the hub, wherein the secondary struts emanate from the first end of the hub and extend therefrom to free ends to centralize the filter in the expanded state in the blood vessel, each secondary strut extending arcuately along the longitudinal axis and linearly radially, each secondary strut having a first arc extending from the connected end away from the longitudinal axis and a second arc extending from the first arc towards the longitudinal axis, the second arc extending to the free end without a hook, the secondary struts having a smaller diameter than the primary struts, each primary strut having two secondary struts in side-by-side relationship with the primary strut, wherein the length of the filter is defined by the first length of the primary struts;

a retrieval hook extending from the hub opposite the plurality of primary and secondary struts for removal of the filter from the blood vessel; and an introducer tube in which the removable filter in the collapsed state is disposed for retrieval or delivery of the filter, the first diameter ranging between about 6 French and 14 French, the second diameter ranging between about 3 French and 9 French.

\* \* \* \* \*